United States Patent
Behl et al.

[11] Patent Number: 5,100,388
[45] Date of Patent: Mar. 31, 1992

[54] METHOD AND DEVICE FOR THERMAL ABLATION OF HOLLOW BODY ORGANS

[75] Inventors: Robert S. Behl, Palo Alto; Colin J. Nichols, Fremont, both of Calif.

[73] Assignee: Interventional Thermodynamics, Inc., Mountain View, Calif.

[21] Appl. No.: 529,077

[22] Filed: May 25, 1990

Related U.S. Application Data

[63] Continuation-in-part of Ser. No. 407,839, Sep. 15, 1989, Pat. No. 5,045,056.

[51] Int. Cl.$^5$ ................................................ A61F 7/12
[52] U.S. Cl. ................................. 604/113; 604/49; 128/401
[58] Field of Search ................. 604/113–114, 604/49; 128/399–401, 784, 786, 804; 606/33

[56] References Cited

U.S. PATENT DOCUMENTS

| | | | |
|---|---|---|---|
| 3,901,224 | 8/1975 | Bucalo . | |
| 4,160,455 | 7/1979 | Law . | |
| 4,375,220 | 3/1983 | Matvias | 128/804 |
| 4,469,103 | 9/1984 | Barrett . | |
| 4,638,436 | 1/1987 | Badger et al. . | |
| 4,676,258 | 6/1987 | Inokuchi et al. . | |
| 4,709,698 | 12/1987 | Johnston et al. | 604/114 X |
| 4,754,752 | 7/1988 | Crinsburg et al. | 604/113 X |
| 4,776,349 | 10/1988 | Nashef et al. | 604/101 X |
| 4,869,248 | 9/1989 | Narula . | |
| 4,945,912 | 8/1990 | Langberg | 128/642 |
| 4,946,440 | 8/1990 | Hall | 604/95 |
| 4,979,948 | 12/1990 | Geddes et al. | 606/33 |
| 4,998,933 | 3/1991 | Eggers et al. | 606/41 |
| 5,007,437 | 4/1991 | Sterzer | 428/786 |

FOREIGN PATENT DOCUMENTS

| | | |
|---|---|---|
| 3725691 | 3/1988 | Fed. Rep. of Germany . |
| 281489 | 9/1970 | U.S.S.R. . |
| 1329781 | 8/1987 | U.S.S.R. . |

OTHER PUBLICATIONS

Coleman, (1988) SCVIR pp. 214–219.
Salomonowitz et al. (1984) Arch. Surg. 119:725–729.
Getrajdman et al. (1985) Invest. Radiol. 20:393–398.
Getrajdman et al. (1986) Invest. Radiol. 21:400–403.
Remley et al. (1986) Inest. Radiol. 21:396–399.
Becker et al. (1988) Radiology 167:63–68.

*Primary Examiner*—C. Fred Rosenbaum
*Assistant Examiner*—C. Maglione
*Attorney, Agent, or Firm*—Townsend and Townsend

[57] ABSTRACT

Hollow body organs, such as the gallbladder, may be ablated by introducing a substantially unheated thermally conductive medium to the interior of the organ. The thermally conductive medium is then heated to a temperature sufficient to necrose the endothelial lining or mucous membrane of the organ. After the lining or membrane has necrosed, the interior of the organ will fibrose over time and the organ will eventually be resorbed by the body. A catheter useful in performing the ablation method comprises an elongate member having a heating element at its distal tip. The catheter will include at least one lumen for delivering the thermally conductive medium to the interior of the hollow body organ, and the heating means is used to raise the temperature of the thermally conductive medium after it has been delivered. Optionally, the catheter may include one or more inflatable balloons which facilitate sealing of the hollow body organ to inhibit leakage of the thermally conductive medium during the treatment process. The heating element may comprise a single point heat source or a heat source distributed over a fixed length. Distributed heat sources may further be adapted to provide for a non-linear heat flux delivery pattern.

59 Claims, 8 Drawing Sheets

METHOD AND DEVICE FOR THERMAL ABLATION OF HOLLOW BODY ORGANS

BACKGROUND OF THE INVENTION

This application is a continuation-in-part of application Ser. No. 07/407,839, filed Sept. 15, 1989, now U.S. Pat. No. 5,045,056 the disclosure of which is incorporated herein by reference.

1. Field of the Invention

The present invention relates generally to methods and apparatus for the thermal ablation of hollow body organs, such as the gallbladder. In particular,. the present invention relates to a catheter structure having a heating element at its distal end, where the catheter may be used to introduce an unheated thermally-conductive medium to the hollow body organ, and the heating element used to heat the medium in situ in order to destroy the endothelial lining or mucous membrane of the organ.

Heretofore, it has frequently been necessary to perform open surgery in order to remove diseased body organs, such as gallbladders, appendixes, and the like. For example, the current treatment for cholecystolithiasis (gallstone disease) involves the surgical removal of the gallbladder, referred to as a cholecystectomy. As with all major surgical procedures, the patient is exposed to the risk of trauma, infection, general anesthetic, as well as requiring extended recuperation time. It would therefore be desirable to provide for therapies for diseased organs which can effectively eliminate the organ without the necessity of open surgical intervention.

In recent years, a number of therapies have been developed as an alternative to open surgery, often referred to as "least invasive surgery." While least invasive surgical procedures have no fixed definition, they are generally characterized by the use of specialized surgical tools in combination with visual or radiographic imaging techniques. The specialized tool is generally inserted through an open body orifice or a small surgical incision, and the tool is then positioned within the body using the imaging technique to allow manipulation of the affected organ or structure. A common example of least invasive surgery is arthroscopic knee surgery where penetration of the surgical tools is minimal. Less accessible body organs, such as the heart and interior blood vessels, may be reached by specialized catheters which may be routed through the vascular system over relatively long distances. Typical of such vascular catheters are balloon dilatation catheters which are used to expand regions of stenosis within diseased blood vessels.

For the above reasons, it would be desirable to provide least invasive surgical methods and apparatus for the destruction or ablation of diseased hollow body organs, such as the gallbladder, the appendix, the uterus, and the like. Such methods and apparatus should also be suitable for the treatment of relatively small body structures, such as blood vessels, and should be able to effect ablation without undue risk to surrounding body tissues and structures. In particular, the method and apparatus should be able to provide for the controlled application of thermal energy in order to destroy the hollow body organ with a minimal chance of regeneration. Desirably, the apparatus should be sufficiently small and flexible to allow introduction through and into constricted ducts and passages adjoining the hollow body organ. and the apparatus should be capable of delivering a non-linear heat flux which varies depending on position within the hollow body organ and/or connecting duct. Such non-linear heat flux will allow control of the amount of heat delivery to particular regions within the organ and/or duct.

2. Description of the Background Art

Coleman, *Non-Surgical Ablation of the Gallbladder*, Proc. 1988 SCVIR, pp 214-219, is a review article discussing various techniques for non-surgical gallbladder ablation, including the work of Salomonowitz and of Getrajdman relating to the introduction of an externally heated medium to induce fibrosis of the gallbladder. The article further presents data demonstrating thermal ablation of a dog's gallbladder after open surgical injection of hot contrast media. The work of Salomonowitz is described in Salomonowitz et al. (1984) Arch. Surg. 119:725-729. The work of Getrajdman is described in Getrajdman et al. (1985) Invest. Radiol. 20:393-398 and Getrajdman et al. (1986) Invest. Radiol. 21:400-403. The use of sclerosing agents to induce gallbladder fibrosis is described in Remley et al. (1986) Invest. Radiol. 21:396-399. See also Becker et al. (1988) Radiology 167:63-68. U.S. Pat. No. 4,160,455, describes a device for internally heating a body cavity for therapy, where the heat is intended to inhibit the growth of tumor cells. German Patent 37 25 691 describes a catheter combining a heater at its distal tip and a balloon proximate the heater, where the heater is not directly exposed to the fluid environment surrounding the catheter tip. U.S. Pat. No. 4,869,248, describes a thermal ablation catheter having a resistive heating loop at its distal end. Other patent documents describing heated or cooled catheters include U.S. Pat. Nos. 4,676,258; 4,638,436; 4,469,103; 4,375,220; 3,901,224; USSR 1329-781-A; and USSR 281489.

SUMMARY OF THE INVENTION

The present invention is a method and apparatus for thermally ablating hollow body organs in order to deactivate the function of the organ, usually by inducing fibrosis of the interior of the organ and eventual resorption of the organ by the body. The method relies on introducing a substantially unheated thermally conductive medium into the interior of the hollow body organ and subsequently heating the medium to a temperature sufficient to destroy the endothelial lining or mucous membrane. Use of an unconstrained media allows heat to be transferred effectively to a convoluted interior surface of the hollow body organ. Usually, some or all ducts, passages, and the like, opening into the hollow body organ will be blocked in order to inhibit leakage of the medium during the treatment procedure. The heating will be stopped after the desired thermal injury has occurred, and the thermally conductive medium may either be aspirated or left within the organ. The organ will in most instances fibrose and be resorbed over time.

The introduction of a substantially unheated thermally conductive medium minimizes the risk of injury to tissue, organs, and other body structures surrounding the hollow body organ being treated, as well as to medical personnel administering the treatment. The use of a radiologically detectable thermally conductive fluid such as contrast media allows visual confirmation that the medium is contained within the desired body organ and is not subject to leakage prior to heating of the medium.

The apparatus of the present invention comprises a catheter including an elongate member having proximal and distal ends with a heating means mounted near the distal end. The heating means is exposed to the fluid environment surrounding the distal end of the catheter and is thus able to directly heat the thermally conductive medium which has been introduced to the hollow body organ. Conveniently, the catheter includes a lumen or other means for introducing the thermally conductive medium. Thus, the catheter may be introduced into the interior of the hollow body organ and utilized both for introducing a thermally conductive medium and for heating the medium to ablate the lining of the organ. Usually, the catheter will also include one or more inflatable balloons or other means for sealing ducts or other passages communicating with the hollow body organ. The catheter is introduced in such a way that the balloons are disposed within the ducts or passages and by then inflating the balloons, the desired sealing of the hollow body organ may be achieved.

Optionally, the catheter may be repositioned during a treatment procedure in order to control the amount of heat delivered to certain regions of the organ and connecting duct(s). In particular, the catheter may first be inserted well into the duct so that a limited amount of heat sufficient to injure the mucosa or endothelial lining of the duct (but not excessive to result in damage to surrounding tissue) may be delivered. The catheter may then be moved to expose the heating element to the main volume of the hollow body organ so that a substantially greater amount of heat may be delivered without causing damage to the tissue surrounding the duct.

In a specific embodiment, the elongate member is flexible to facilitate introduction into the hollow body organ and optionally into connecting ducts and passages. The heating means is located proximally or distally to the balloon or other sealing means and extends over a predetermined length, typically at least about 3 mm, usually from about 3 mm to 6 cm, more usually from about 1 cm to 4 cm, and most usually from about 1.5 cm to 3 cm. To further facilitate introduction and placement of the catheter, the heating means is adapted to conform to the flexure of the elongate member, where such flexibility is of particular advantage when the catheter is to be placed into relatively constricted ducts or passages which connect with the hollow body organ. Flexible heating means able to conform to bending of the elongate member may comprise a coil heating element, a series of relatively small, discrete heating elements distributed over said predetermined length, or the like.

In a preferred aspect of the present invention, the heating means is further adapted to deliver a non-linear heat flux pattern over its axial length. The heat flux pattern, in turn, may be selected to provide a desired heating profile within the fluid environment surrounding the distal end of the catheter. In this way, heating of the fluid environment may be "programmed" to provide the proper amount of heat to each region within the hollow body organ and optionally the connecting duct(s). Usually, a lesser heat flux will be directed within small regions, such as a connecting duct, where the reduced volume of the fluid environment will allow the desired treatment temperature to be attained with the application of less heat. Greater heat flux may be simultaneously provided to the larger regions of the hollow body organ which require greater total amounts of heat to reach the desired treatment temperature. Treatment of both the hollow body organ and connecting region(s) may thus be performed in a single step without the need to reposition the catheter.

DESCRIPTION OF THE SPECIFIC EMBODIMENTS

The present invention is useful for ablation of a wide variety of hollow body organs and body passages which have an endothelial lining, mucous membrane, or other internal surface which may be thermally injured to inactivate the organ and usually to induce necrosis and subsequent fibrosis of the surrounding tissue. Exemplary hollow body organs include the gallbladder, the appendix, the uterus, the kidney, and the like. Exemplary hollow body passages include blood vessels, fistulas, and the like. Usually, the hollow body organs and body passages will be diseased or in some way abnormal prior to ablation according to the present invention. In some cases, however, it may be desirable to ablate and destroy apparently healthy body organs or parts in order to achieve a desired purpose, e.g., blockage of a blood vessel in a varicocele procedure. For convenience hereinafter, the phrase "hollow body organ" is intended to embrace both hollow body organs and hollow body passages.

The method of the present invention relies on introducing a thermally conductive medium into the interior of the hollow body organ in such a way that the organ is filled with the medium and the medium is in good thermal contact with substantially the entire interior surface of the organ. In this way, by heating the medium as will be described hereinafter, the temperature of the endothelial lining or mucous membrane of the body organ can be raised to a preselected temperature for a preselected minimum time period in order to permanently injure the lining and deactivate the organ, typically by inducing necrosis. The thermally conductive medium can be virtually any physiologically-compatible liquid, solution, slurry, gel, and the like, which may be percutaneously or directly introduced into the interior of the hollow body organ. Exemplary thermally conductive media include water, saline, contrast medium, physiological irrigating solution, and the like.

A used herein, the term "ablation" means any injury or damage to the hollow body organ and/or connecting ducts and body passages which results in deactivation of the function of the organ, usually resulting in necrosis and eventual resorption of the organ. The resorption will typically occur over an extended period of weeks, months, or longer.

The thermally conductive medium will be introduced to the interior of the hollow body organ at a temperature below that which will have a deleterious effect on the tissue and organs surrounding the hollow body organ being treated. The temperature will be below about 60° C., usually being below about 45° C., and more usually being at body temperature (37° C.) or room temperature (about 20° C.). In some cases, however, it may be desirable to introduce the contrast medium above body temperature, usually in the range from about 37° C. to 45° C., in order to shorten the time necessary to raise the temperature of the medium to the treatment temperature, discussed hereinafter.

In order to induce necrosis of the endothelial lining or mucous membrane of the hollow body organ, the temperature of the thermally conductive medium will be raised and maintained above a threshold level which results in injury to the endothelial mucous membrane. The threshold temperature will generally be above 45° C., usually being in the range from 45° C. to 120° C., more usually being in the range from 65° C. to 100° C., and preferably being in the range from about 70° C. to 90° C. Depending on the precise temperature employed and on the nature of the particular organ being treated, the thermally conductive medium will be maintained above the threshold temperature for a period of time in the range from about 1 to 60 minutes, usually being in the range from about 1 to 30 minutes, more usually being in the range from about 2 to 20 minutes, and preferably being in the range from about 2 to 10 minutes. Usually, the temperature of the thermally conductive medium will be raised as rapidly as possible and maintained at a substantially constant treatment temperature for the desired treatment period. Alternatively, the treatment temperature may be varied during the treatment period with the total treatment time being adjusted to take the variation in temperature into account.

Frequently, it will be desirable to control the amount of heat or heat flux being delivered to any particular region within the hollow body organ and connecting duct(s) being treated. It will be appreciated that the temperature of the thermally conductive medium within the organ is a function of both the heat flux being delivered and the volume of thermally conductive medium surrounding the area where heat is being applied. Thus, for hollow body organs which have a non-uniform cross sectional area, the volume will vary over the length of the organ and the temperature at any given point within the medium may deviate substantially from the average. In some cases therefore, it will be desirable or necessary to control the rate of heat being delivered (i.e. heat flux) at any particular location within the hollow body organ and connecting duct(s) to assure that the temperature within the desired range is reached (either simultaneously or at different times) at all locations being treated. As described in more detail hereinafter, such controlled or programmed heat delivery may be accomplished by positioning a relatively small heating element for different amounts of time at various locations within the hollow body organ in order to attain generally uniform heat treatment throughout. Alternatively, by employing a heat delivery system which can provide for a non-linear heat flux over at least a portion of the length, uniform heat treatment of the hollow body organ can be obtained in a single application of heat without repositioning the catheter.

After the hollow body organ has been treated with the heated thermally conductive medium at a temperature and for a time sufficient to deactivate the body organ and/or induce necrosis of the endothelial lining or mucous membrane of the organ, the thermal energy being delivered to the medium will be terminated. The thermally conductive medium may then be aspirated from the hollow body organ, typically using the same catheter which was employed to deliver the medium and raise the temperature of the medium as described above. Usually, however, the thermally conductive medium will not be aspirated until the temperature has decreased sufficiently so that its withdrawal will not expose tissues and organs surrounding the catheter to risk. Normally the withdrawal temperature will be below about 55° C., preferably being below about 45° C. Alternatively, the thermally conductive medium can be left within the hollow body organ where it will be resorbed or eliminated by normal physiological processes.

The catheter of the present invention comprises an elongate member having proximal and distal ends. The elongate member may be flexible or rigid, although flexible catheters are preferred for most applications. The length of the catheter will vary depending on the application with short, rigid catheters typically having a length in the range from about 10 to 20 cm, and long flexible catheters typically having a length in the range from about 20 to 40 cm. Rigid elongate members may be formed from metals, typically stainless steel, rigid plastics, and the like, while flexible elongate members will typically be formed from extruded organic polymers, such as silicone rubber, polyurethane, polyvinyl chloride, nylon, and the like. Elongate members will typically include a multiplicity of lumens to provide for fluid communication between the proximal end (outside the patient) to the distal end (inside the patient). Normally, a lumen will be provided for delivering and/or aspirating the thermally conductive medium to the hollow body organ. Additional lumens may be provided for inflation of one or more balloons, for delivery of the catheter over a movable guidewire, for venting the hollow body organ while the thermally conductive medium is being delivered, and the like.

A heating means for raising the temperature of the fluid environment surrounding the distal end of the catheter will be provided at or near the distal tip of the elongate member typically being within about 10 cm, more typically being within about 5 cm. The heating means will generally provide a heated surface for convectively heating fluid surrounding the catheter tip, typically comprising a resistive heater, a radiating block heated by laser energy, or the like. Preferably, the heated surface will be exposed directly to the environment surrounding the catheter, with a minimum amount of insulation covering the surface, in order to enhance heat transfer. The heating means may alternatively comprise a microwave emitter capable of heating the fluid directly or a radiofrequency heating element. In some cases, it may also be possible to heat the thermally conductive medium using dispersed laser radiation. In that case, it will be desirable to color or dye the thermally conductive medium so that it can absorb radiation at the wavelength of the laser source.

A system will be provided for controlling the temperature to which the thermally conductive medium is heated by the heating means. Such a temperature control system may comprise a feedback controller where a temperature sensing element (typically a thermocouple or thermistor) is mounted on the catheter at a location chosen to accurately measure the heated environment surrounding the catheter, and the energy delivered to the heating means is regulated based on the measured temperature of the medium. Alternatively, numerous autoregulating heaters are available which do not require a separate control loop.

The heating means may comprise a single point heating source, for example a single cartridge heater, extending over a limited distance, usually 3 mm or less. Often, however, it is desirable to provide a distributed heating source over an extended axial length greater than 3 mm, usually being in the range from from about 3 mm to 6 cm, more usually being in the range from about 1 cm to 4 cm, and most usually being in the range from about 1.5 cm to 3 cm. Such elongate heating sources will preferably be flexible over their length when mounted on flexible elongate members. In this way, the desired flexibility of the catheter will not be substantially diminished by the heating source. In particular, the heating source itself will be able to be inserted into constricted, relatively tortuous, ducts and passages connecting with the hollow body organ.

Flexible elongate heating sources will typically comprise either a plurality of spaced-apart discrete heating elements, e.g. a plurality of single point heating sources such as cartridge heaters, or a continuously wound heating source, such as a heating coil wrapped around the exterior of the flexible elongate member. In either case, it will often be desirable to adapt the axially elongated heating source to deliver a variable heat flux over its length. In particular, the heat flux may be reduced in regions where the heating source will be within a restricted volume of thermally conductive medium and relatively increased where the heating source will be in a larger volume of thermally conductive medium. In this way, a relatively uniform temperature profile within the hollow body organ and optionally connecting ducts may be achieved.

Usually, the catheter will include at least one inflatable balloon for occluding a duct or passage which would otherwise allow drainage of the thermally conductive medium from the hollow body organ during the course of the treatment. At least one balloon will generally be located near the distal tip of the elongate member of the catheter and will be inflatable through an inflation lumen running through the catheter from the distal to the proximal end thereof. For many applications it will be desirable to inflate the occluding balloon with a thermally conductive medium, frequently the same medium used to fill the hollow body organ, so that the area in contact with the balloon will be heated and necrosed. Optionally, means for heating the medium within the balloon to a temperature sufficient to induce necrosis in the endothelial lining or mucous membrane surrounding the inflated balloon may be provided. Such heating means may be formed separately from or together with the means used to heat the unconstrained thermally conductive medium. Alternatively, a thermally insulating medium such as carbon dioxide may be used to inflate the balloon when it is desired to protect the surrounding tissue and organs.

One or more additional inflatable balloons may also be provided in order to seal other passages communicating with the hollow body organ. For example, a second inflatable balloon may be located on a side of the heating element opposite to that of the first heating element. The first and second balloons may then be used to define a volume to be treated therebetween. Other balloon configurations may also be used for trapping the thermal media in a particular hollow body organ or portion of a hollow body organ.

Although inflatable balloons will find the greatest use, other means for sealing or occluding a connecting duct or region may also be utilized. In particular, it will be possible to modify the distal tip of the catheter so that it may be lodged within the duct or region to provide the desired seal. For example, the tip may be tapered or expanded so that it will conform to the geometry of the duct or passage. Other modifications may be based on the geometry of the organ being treated.

Referring now to FIGS. 1-4, a catheter 10 comprises an elongate flexible body 12 having a proximal end 14 and a distal end 16. The elongate member 12 includes a plurality of axial slots 18 formed at or near the distal end 16 and a heating element 20 disposed within the slots. The heating element 20 is of a type which provides a heated external surface, typically being a resistive heating element where a pair of wires 22 are run from the heating element to the proximal end 14 of the catheter where they are taken out through a sealed port 23 in a proximal housing 24. The wires 22 will typically be run through a central lumen 26 and will be connected to a suitable power supply (not shown) for heating the heating element 20 to a desired temperature.

Figure 1:
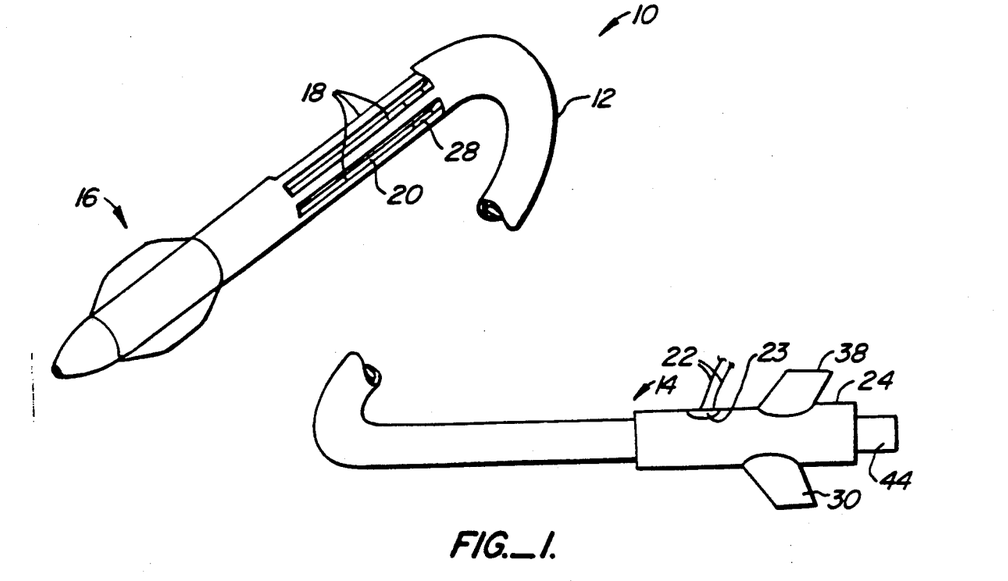
FIG. 1 is a perspective view of a thermal ablation catheter constructed in accordance with the principles of the present invention.
Figure 2:
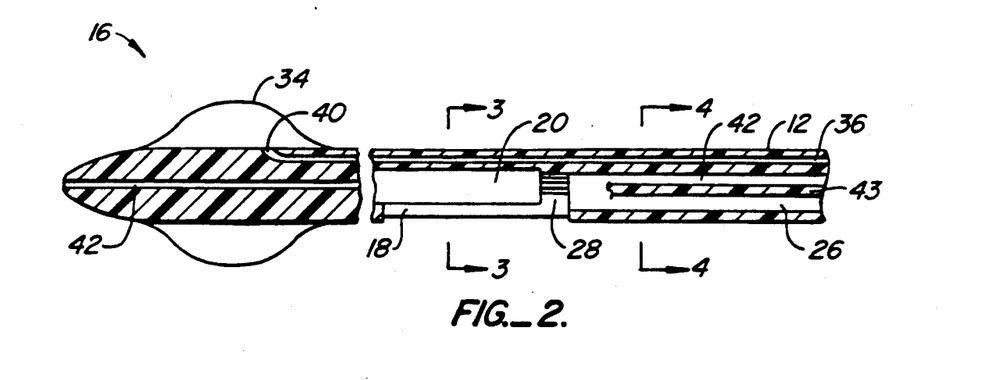
FIG. 2 is a detailed elevational view of the distal end of the catheter of FIG. 1 shown in cross-section.
Figure 3:
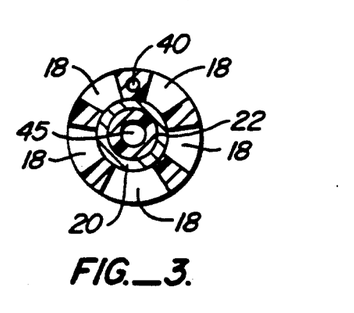
FIG. 3 is a cross-sectional view taken along line 3—3 of FIG. 2.
Figure 4:
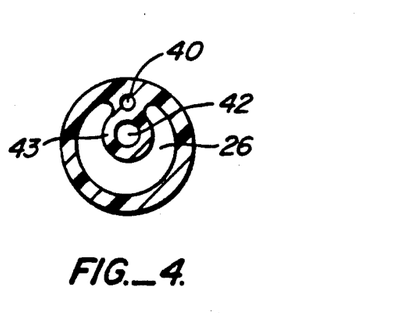
FIG. 4 is a cross-sectional view taken along line 4—4 of FIG. 2.

The central lumen 26 extends from the proximal end 14 of the elongate member 12 and terminates at the proximal end of heating element 20 (FIG. 2). A plurality of radial passages 28 (FIG. 2) are provided between the distal end of the central lumen 26 and the proximal end of the heater 20, which passages open into the axial slots 18. The proximal end of central lumen 26 is connected through a side port 30 on the proximal housing 24. In this way, thermally conductive medium may be delivered through the central lumen 26 past the heating surface of heating element 20 and into the hollow body organ. The thermally conductive media is thus rapidly heated as it passes the heater 20 into the hollow body organ.

The catheter 10 also includes an inflatable balloon 34 at its distal tip. The balloon 34 may be inflated through inflation lumen 36 which extends from an inflation port 38 on housing 24 to an outlet port 40 communicating directly with the interior of the balloon 34. The balloon 34 will usually be inflated with a heat conductive medium which will be heated by conduction from the heated fluid trapped by the balloon within the hollow body organ. An optional system (not illustrated) for heating the balloon within the medium may be provided. Systems for heating inflation medium within a balloon are described in U.S. Pat. No. 4,754,752, the disclosure of which is incorporated herein by reference.

A third lumen 42 is formed in a tubular extension 43 disposed in central lumen 26. Lumen 42 extends through the distal tip of the catheter 10 and is axially-aligned with a lumen 45 (FIG. 3) through the heater 22. The tubular extension 43 is usually separated from the main portion of flexible body 12 and attached to the heater (not illustrated) to allow thermally conductive fluid to flow unobstructed from the central lumen 26 past the heater 22 and through the slots 18. Together, the lumens 42, 43, and 45 are intended to form a fluid tight passage which can receive a movable guidewire which can be used to facilitate placement of the catheter 10 within the desired hollow body organ, as described in more detail hereinafter.

Figure 9:
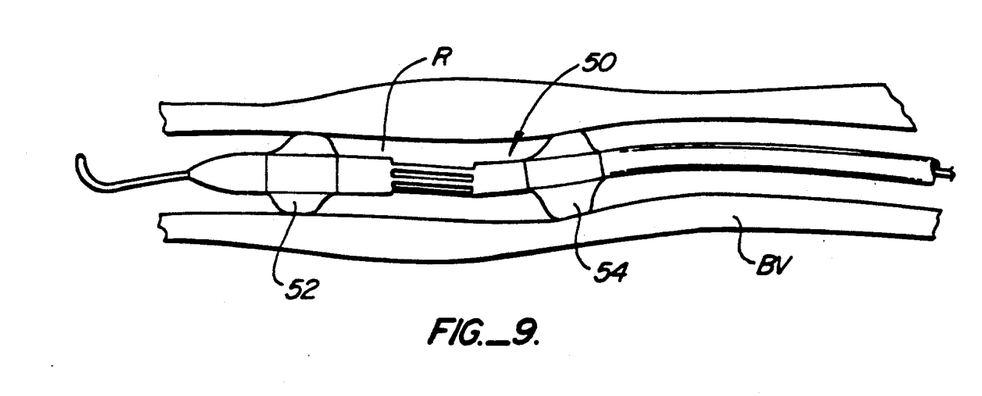
FIG. 9 illustrates the method of the present invention used in the thermal ablation of a segment of a blood vessel.

Referring now to FIGS. 5-7 and 9, a catheter 50 which is similar to catheter 10 but includes a pair of spaced-apart inflation balloons 52 and 54 is illustrated. The catheter 50 includes an elongate flexible member 56, a heating element 58, and is generally constructed as described previously for catheter 10. The catheter 50, however, includes the second inflatable balloon 54 which is spaced-apart proximally from the first balloon 52, with the two balloons being disposed on opposite sides of heating element 58. In this way, the two balloons 52 and 54 are able to isolate a volume therebetween which includes the heater 58. By introducing the thermally conductive medium between the two balloons 52 and 54, the heater 58 may then be used to heat the isolated medium in treating a desired portion of a hollow body organ. The catheter 50 includes first inflation lumen 60 to inflate the first balloon 52 and a second inflation lumen 62 to inflate the second balloon 54. A central lumen 64 serves both to introduce thermally conductive medium and to receive a guidewire to facilitate placement of the catheter. The guidewire may be received in a tubular extension (not illustrated) or a seal, such as an O-ring, may be provided to inhibit leakage of medium. Use of catheter 50 to ablate a region within a blood vessel BV is illustrated in FIG. 9. Such ablation will be useful in terminating the blood supply to a tumor, or to an arteriovenous shunt, or in other procedures where it is desired to block a blood vessel.

Figure 5:
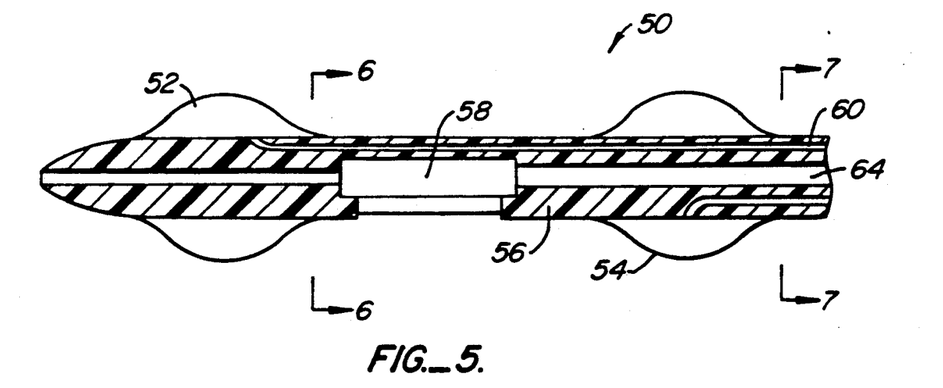
FIG. 5 is a detailed elevational view of the distal end of the catheter having two inflation balloons spaced-apart at its distal end shown in cross-section.
Figure 6:
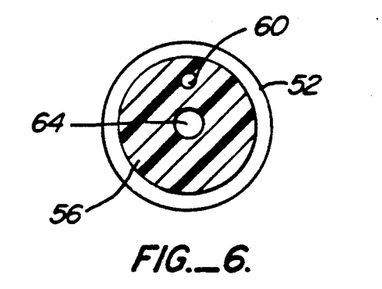
FIG. 6 is a cross-sectional view taken along line 6—6 of FIG. 5.
Figure 7:
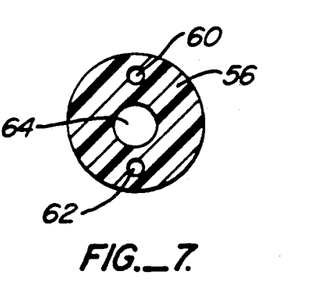
FIG. 7 is a cross-sectional view taken along line 7—7 of FIG. 5.

Referring now to FIGS. 8A-8H, the use of a two-balloon catheter of the type illustrated in FIG. 5 for ablating a gallbladder will be described. Gallbladder ablation will be desirable in cases of cholecystolithiasis where the diseased gallbladder is likely to continue production of gall stones. Gallbladder ablation according to the present invention will generally be performed after the removal of gall stones by established least invasive procedures, typically by either percutaneous cholecystostomy or by lithrotriptor.

Figure 8A:
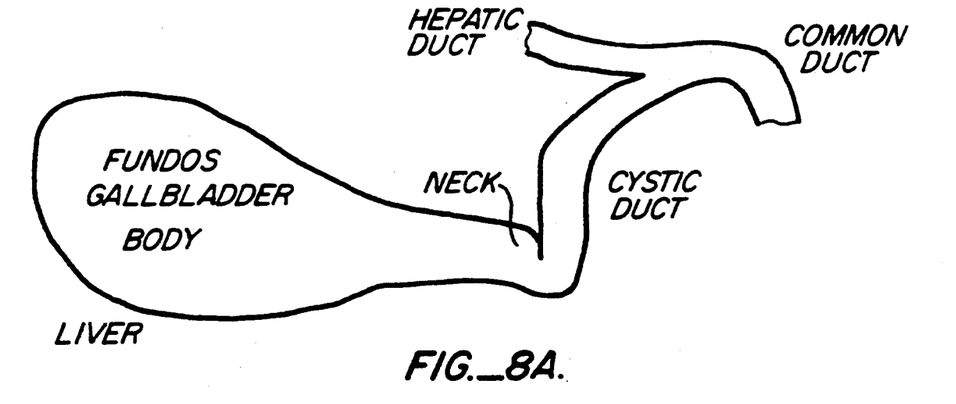
FIGS. 8A–8H illustrate the method of the present invention used in the thermal ablation of a gallbladder.
Figure 8B:
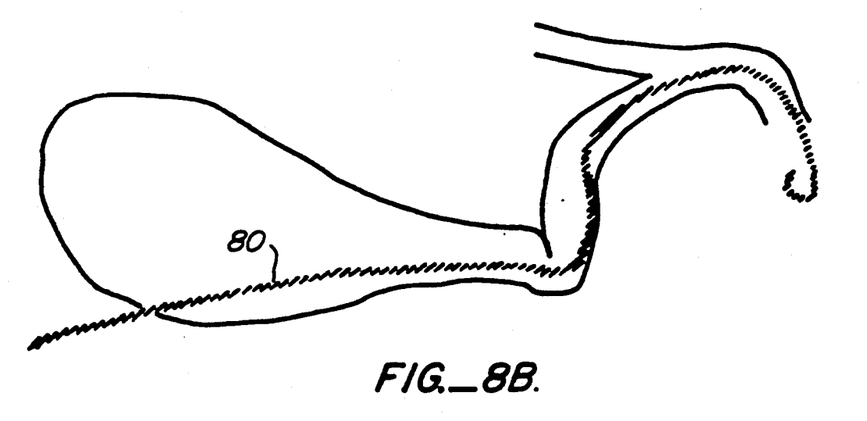
Figure 8C:
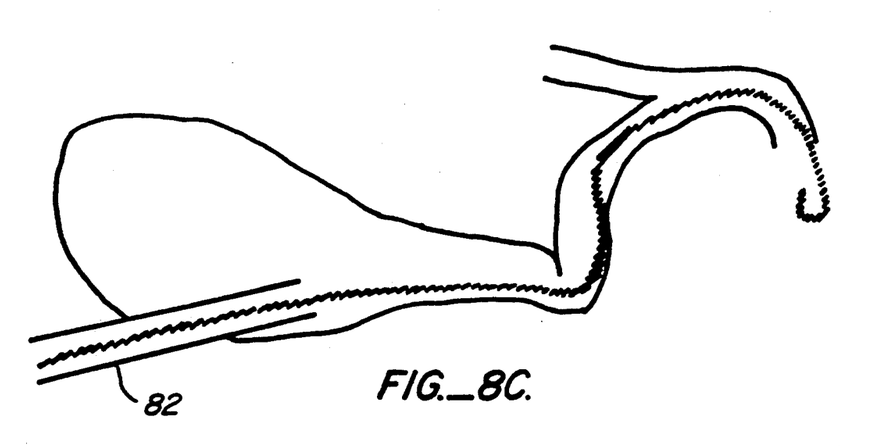

The intact gallbladder is illustrated in FIG. 8A and includes a hollow sac structure connected to the cystic duct through the neck of the gallbladder. The cystic duct, in turn, is connected to the hepatic duct and common bile duct. The gallbladder is located on the lower (inferior) surface of the liver in a hollow (fossa) beneath the right lobe. The upper (superior) surface of the gallbladder is attached to the liver by connective tissue.

Figure 8D:
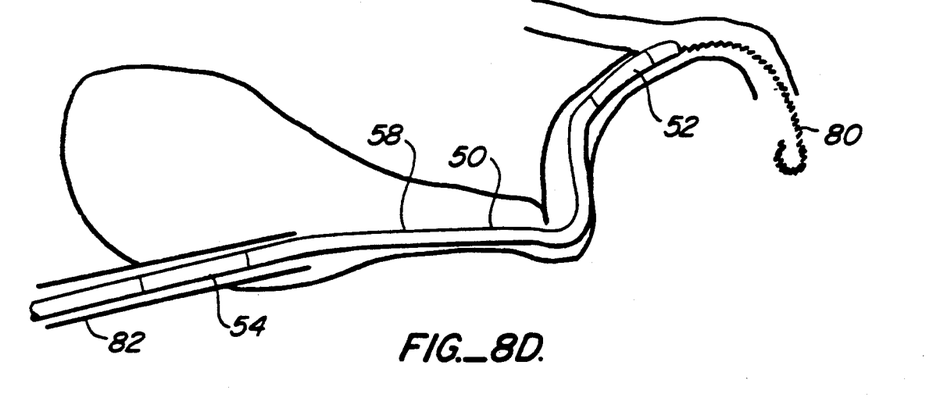

In treating the gallbladder according to the method of the present invention, a percutaneous guidewire 80 (FIG. 8B) is inserted into the gallbladder through the trans-hepatic route and into the common bile duct. A sheath 82 (FIG. 8C) is then placed over the guidewire 80 to provide for access into the interior of the organ. The catheter 50 may then be inserted over the guidewire 80 and positioned so that the first balloon 52 lies beyond the neck of the gallbladder and just proximal to the junction between the hepatic duct and the common duct (FIG. 8D). The second balloon 54 will remain within the sheath 82, while the heater 58 is located within the main body of the gallbladder.

Figure 8E:
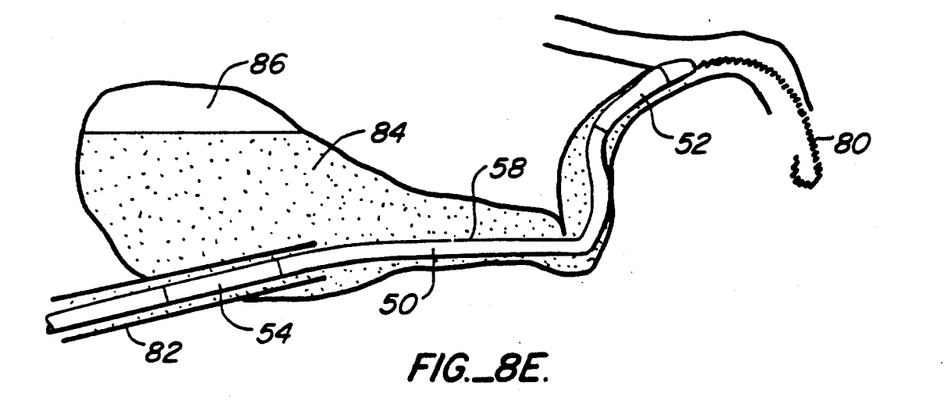
Figure 8F:
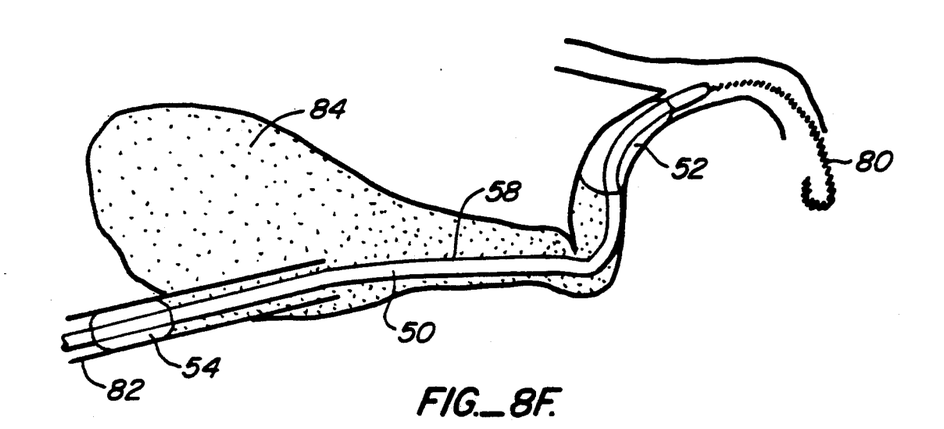

After the catheter 50 is in place, the thermally conductive medium 84 is introduced into the interior of the gallbladder through the catheter (FIG. 8E). The medium 84 is introduced until the main sac is entirely filled, as illustrated in FIG. 8F, and the first and second balloons 52 and 54 are inflated in order to inhibit loss of the medium through the cystic duct and the sheath 82. During the introduction of the thermally conductive medium to the gallbladder, it may be necessary to adjust the position of the patient in order to expel trapped gases 86 (FIG. 8E). The gases 86 may be released through either the cystic duct or the sheath 82, or may be vented through a specially provided vent (not illustrated) within the catheter 50.

Figure 8G:
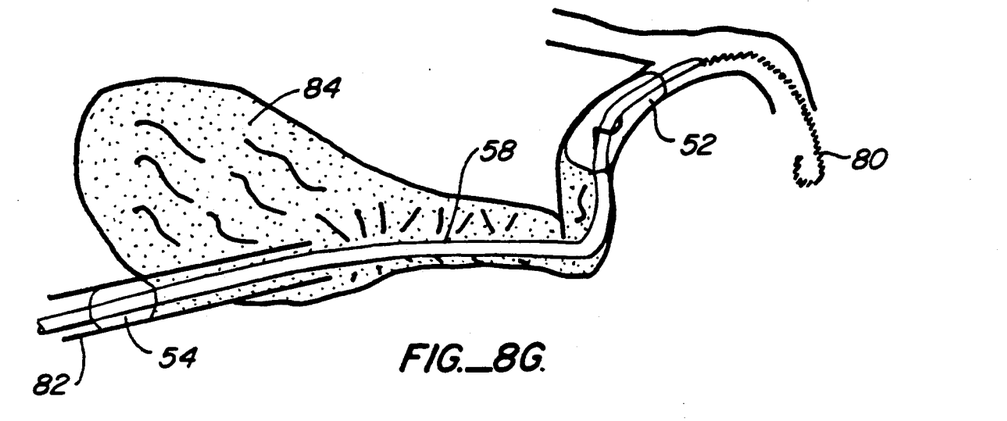

Once the main sac of the gallbladder is completely filled with thermally conductive medium 84 (which may be confirmed by fluoroscopic examination if a radiopaque medium is used), the heating element 58 will be activated to raise the temperature of the medium, either by convection, radiation, or high frequency heating (FIG. 8G). Optionally, the thermally conductive medium 84 may have been partially heated by the heating element 58 as the medium is introduced by the catheter 50. Heat will be conducted from the interior of the organ through the thermally conductive media in the first balloon 52 in order to necrose the mucosa of the cystic duct in order to assure that the gallbladder lining will not regenerate. Usually, the second balloon 54 will be inflated with a thermally insulating medium to protect the liver from the heat of the medium 84.

After maintaining the temperature of the heat conductive medium 84 (and optionally the inflation medium with balloon 52) at the desired ablation temperature for a sufficient time to completely necrose the mucosa of the gallbladder, the heating element 58 may be deenergized.

Figure 8H:
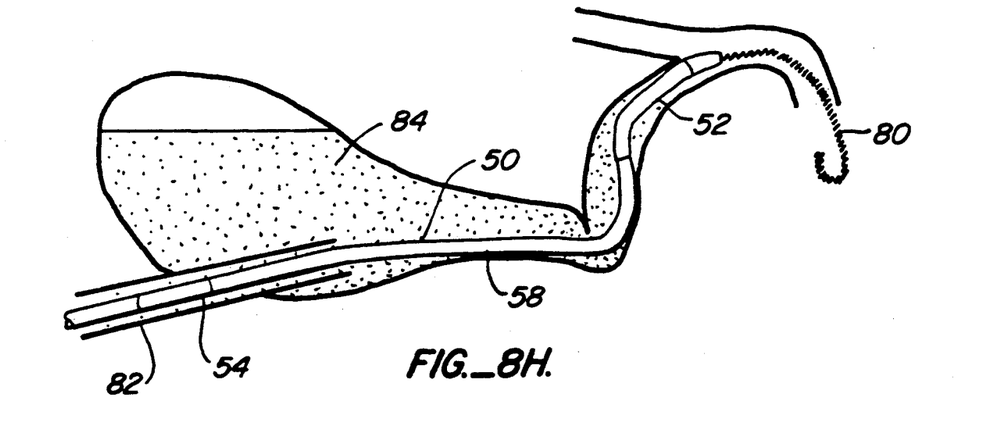

After allowing cooling, the thermally conductive medium 84 may be aspirated through the catheter or optionally through the sheath 82 after balloon 54 has been deflated (FIG. 8H). Alternatively, the thermally conductive medium 84 may be left within the main sac of the gallbladder from which it will eventually drain through the cystic duct and be eliminated by normal physiologic processes.

After about six weeks, the endothelial lining of the gallbladder will be completely necrotic. The inflammation process will completely replace the lining of the gallbladder with fibrotic tissue within about twelve weeks and the organ will start to resorb.

Figure 10:
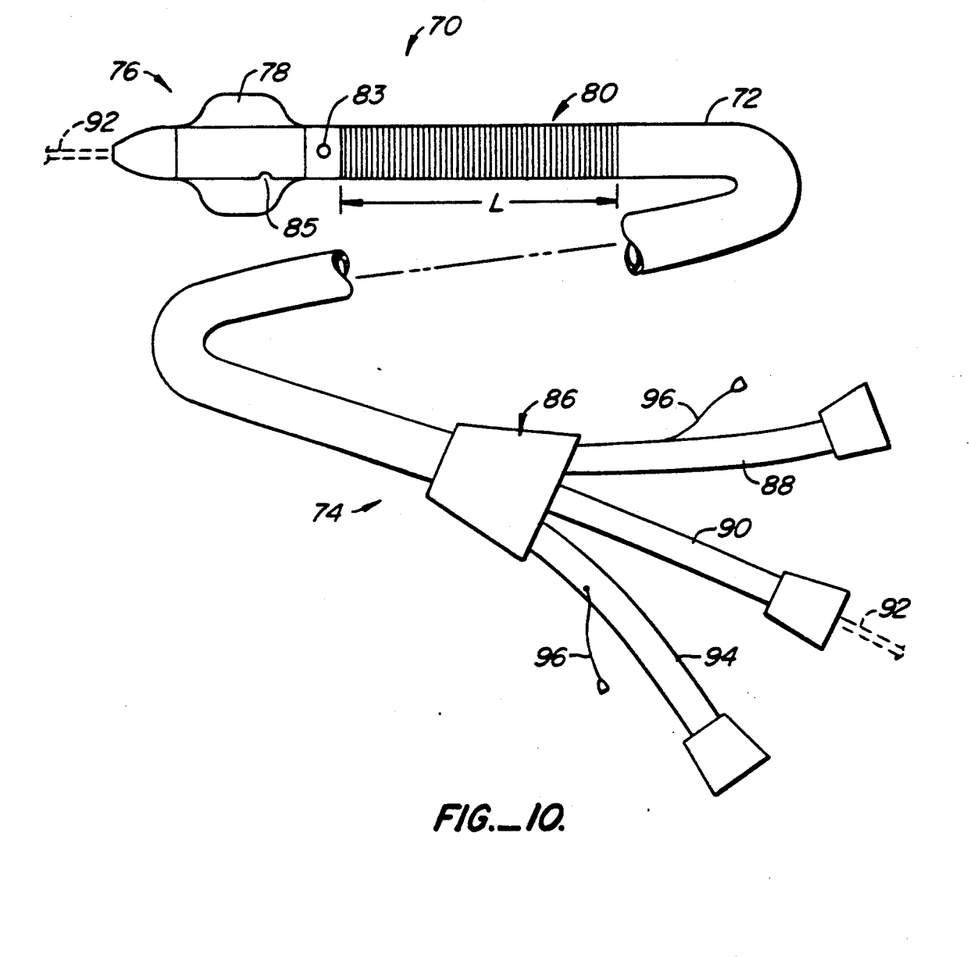
FIG. 10 is a perspective view of a thermal ablation catheter having a flexible heating source constructed in accordance with the principles of the present invention.

Referring now to FIG. 10, the construction of an alternative embodiment 70 of the thermal ablation catheter of the present invention will be described. The catheter 70 is constructed similarly to the catheter 10, described above, and includes an elongate flexible member 72 having a proximal end 74 and a distal end 76. An inflatable balloon 78 is disposed at the distal end 76 of the elongate member 72, and a heating source 80 is located proximal to the balloon 78. The heating source 80 is axially elongated and will be disposed over the exterior of the member. The heating source 80 will cover an axial length L of at least about 3 mm, usually being in the range from about 3 mm to 6 cm, more usually being in the range from about 1 to 4 cm, and will most usually be in the range from about 1.5 cm to 3 cm. A perfusion port 83 is provided between the balloon 78 and heating source 80 to deliver a thermally conductive medium to the hollow body organ during a treatment procedure. The location of the perfusion port is not critical, and the port, for example, could also be located on the proximal side of heating source 80, or elsewhere so long as it is able to deliver thermally conductive medium to a desired location in the body organ and/or connecting region(s). A balloon inflation port 85 is provided interiorly to balloon 78 in order to allow inflation of the balloon.

Fitting 86 is provided at the proximal end 74 of elongate member 72. Fitting 86 includes a first connector 88 which is fluidly coupled to balloon inflation port 85 through an inflation lumen (not illustrated) in the elongate member 72. A second connector 90 is provided for inserting a guidewire 92 through a central guidewire lumen (not illustrated) in elongate member 72. A third connector 94 is connected to perfusion port 83 through a third lumen (not illustrated) in the elongate member 72. Additionally, power leads 96 are provided for connecting heat source 80 to an external power source (not illustrated) typically a current source for powering the resistance heater.

The heating source 80 is formed as an exterior winding or coil on the distal end 76 of the elongate member 72. Typically, the coil 80 will be helically wound, but other patterns will also be suitable. The windings will conveniently be formed from insulated resistance heating wire, where the biocompatible insulation is selected to be able to withstand the physiologic conditions present in the hollow body organ being treated. The total length, number of turns in a particular location, electrical resistivity, and the like, of the wire used for the coil will be selected to provide the desired heating flux delivery capability for the heating source 80. As illustrated, the windings of heating source 80 are uniform over the entire length L, but it will also be possible to provide for a non-uniform winding density when it is desired to vary the heat flux delivery capability over the length of the heat source.

Figure 11:
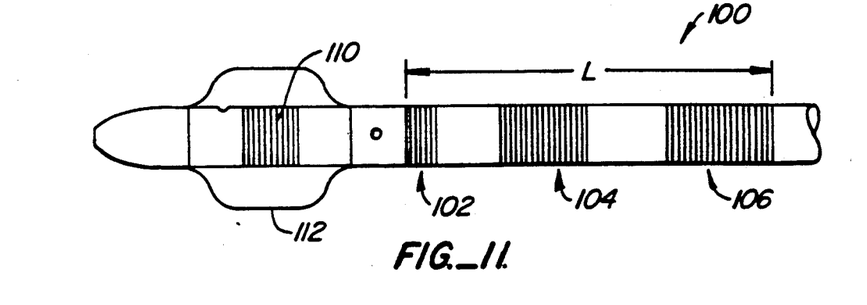
FIG. 11 is an elevational view of the distal end of a thermal ablation catheter having a heating source capable of delivering a non-linear heat flux over its length.

Referring now to FIG. 11, a particular embodiment 100 intended for non-linear heat flux delivery is illustrated. Catheter 100 includes a plurality of spaced-apart coils 102, 104, and 106, over length L. As illustrated, coil 102 located closest to the distal end of catheter 100 includes the fewest windings, with coil 104 having more windings, and coil 106 having the most windings. In this way, the heat flux delivered by catheter 100 will increase over length L in the proximal direction. Such heat flux delivery could be programmed in the opposite way so that the flux will increase in the distal direction, or it could be programmed in virtually any other desired pattern. It would also be possible to use other types of heat sources, such as point sources including cartridge heaters.

A heater 110 is provided within an inflation balloon 112. In this way, heat flux may be provided through the inflatable balloon 112 to the surface of a duct or connecting passage which is being blocked. By properly balancing the heat flux delivery within balloon 112 with the heat flux delivery proximal to balloon 112, simultaneous ablation of a hollow body organ and connecting duct or passage may be achieved in a single treatment step.

Figure 12:
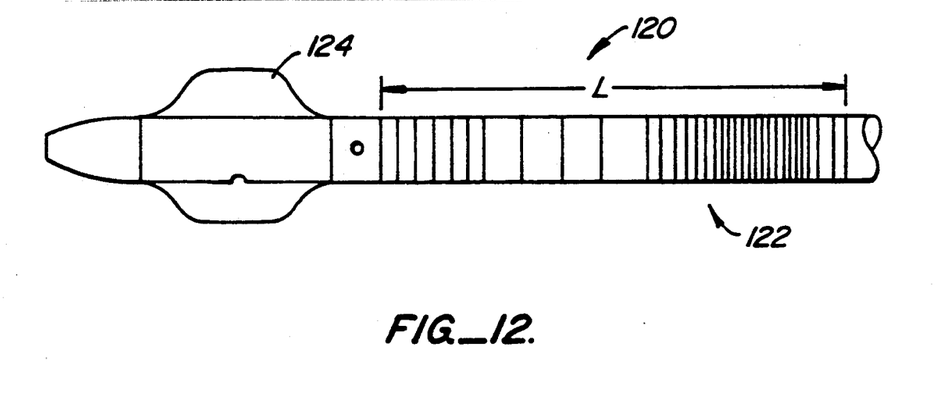
FIG. 12 is an elevational view of the distal end of an alternative embodiment of a catheter having a heat source capable of delivering a non-linear heat flux.

An alternative embodiment 120 of a catheter capable of delivering a non-linear heat flux is illustrated in FIG. 12. Instead of discrete, spaced apart coils as illustrated in FIG. 11, catheter 120 includes a continuous coil 122 over length L, where the coil has a variable helical pitch. By properly selecting the pitch, the heat flux at any point along length L can be selected to accommodate the intended use of catheter 120. Although no heater is illustrated within inflation balloon 124 in catheter 120, a heat source could be provided, either as extension of heating coil 122 or as a separate heating element.

Figure 13:
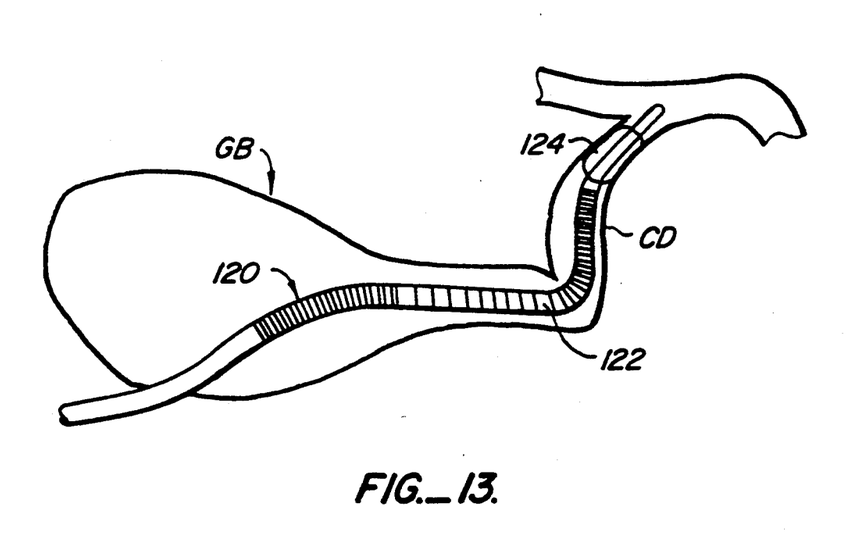
FIG. 13 illustrates the method of the present invention utilizing the catheter of FIG. 12 in ablating a gallbladder and a portion of the connecting cystic duct.

The use of catheter 120 in the ablation of a gallbladder GB is illustrated in FIG. 13. The catheter 120 is introduced into the gallbladder GB and connecting cystic duct CD in a manner similar to that described in connection with FIGS. 8A–8H. The catheter 120 is inserted so that balloon 124 extends well into the cystic duct CD, with the heating coil 122 extending from just proximally of the balloon 124 through the constricted region of the cystic duct CD and into the main body of the gallbladder GB. The pitch of heating coil 122 is varied so that a reduced heat flux will occur within the reduced diameter regions of the cystic duct and an increased heat flux will occur in the larger volumes of the gallbladder body. In this way, the catheter 120 may be positioned, as illustrated, with heat applied along the entire length of the heating coil 122 for a fixed period of time. At the end of the fixed period of time, the proper total amount of heat will be applied to each region within the gallbladder GB and connecting cystic duct CD so that the mucosa will be injured without excessive heat having been applied to any localized area. The catheter 120 may then be withdrawn, either with or without removal of the thermally conductive medium.

Figure 14:
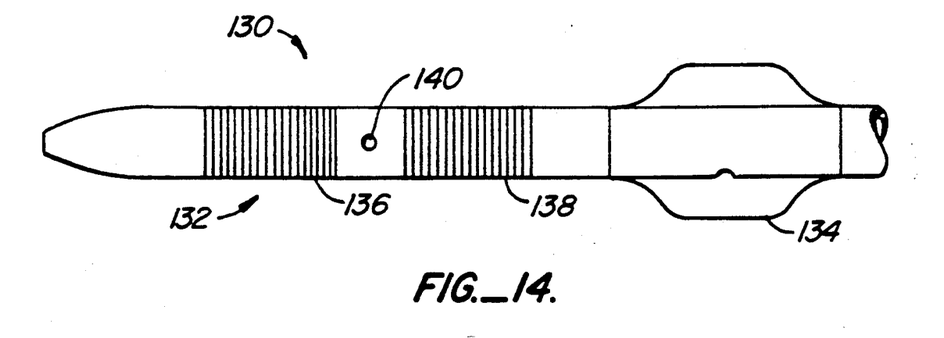
FIG. 14 is an elevational view of the distal end of a thermal ablation catheter having a single inflatable balloon disposed proximally of the heating element.

Referring now to FIG. 14, an additional embodiment 130 of the thermal ablation catheter of the present invention is illustrated. The catheter 130 includes a heating coil 132 disposed distally to an inflatable balloon. Such a construction which includes only a single balloon proximal to the heating element is particularly suitable for retrograde introduction into a hollow body organ, as will be described in connection with FIG. 15. The heating coil 132 is divided into two sections 136 and 138 with a perfusion port 140 located therebetween. The specific design of the heating coil, location of the perfusion port, dimensions of the catheter, and the like, may of course all be varied within the broad parameters described above. FIG. 14 is provided primarily to illustrate an embodiment where the heat source is located distally to a single sealing means.

Figure 15:
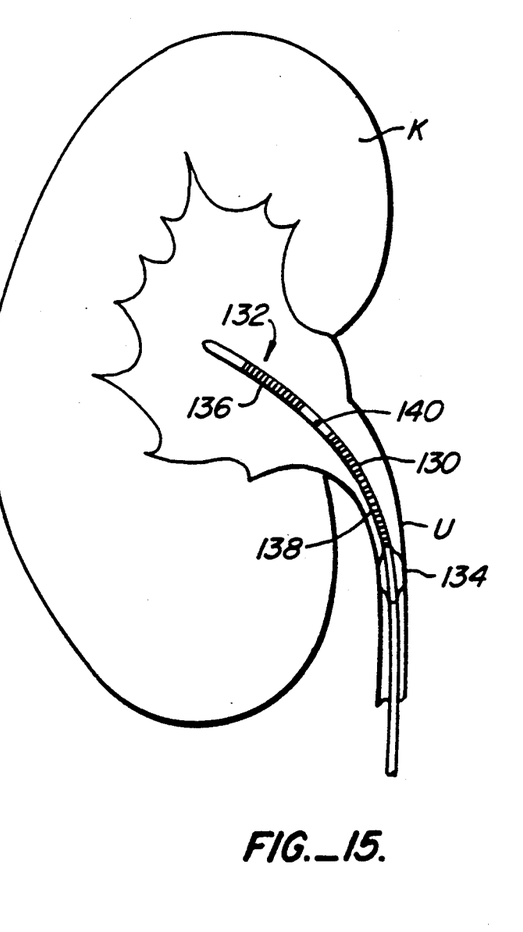
FIG. 15 illustrates the method of the present invention utilizing the catheter of FIG. 14 for ablating a kidney and portion of the connecting ureter.

Catheter 130 is particularly suited for retrograde introduction to a hollow body organ through a connecting region or duct. In FIG. 15, catheter 130 is introduced into a kidney K through the ureter U, where balloon 134 is positioned well back within the ureter while heating element 132 extends into the interior of the kidney. In particular, the distal heating section 136 is located primarily within the kidney, while the proximal heating section 138 remains generally within the ureter. By properly sizing the respective heat outputs of each section 136 and 138, the catheter 130 can be used to simultaneously ablate both the kidney and the exposed portion of the ureter in a single heating step. Conveniently, the perfusion port 140 is located to introduce thermally conductive medium evenly into both the kidney and the ureter.

Although the foregoing invention has been described in detail for purposes of clarity of understanding, it will be obvious that certain modifications may be practiced within the scope of the appended claims.

What is claimed is:

1. A thermal ablation catheter, said catheter comprising:
    a flexible elongate member having proximal and distal ends;
    means for heating an unconstrained environment surrounding the catheter, said heating means comprising a resistive heating element which is exposed directly to the environment over a predetermined length of the elongate member and which is capable of conforming to flexure of the elongate member; and
    a pair of conductors extending from the proximal end of the flexible elongate member to the resistive heating element, whereby the resistive heating element may be connected in a circuit to a power supply.

2. A thermal ablation catheter as in claim 1, further comprising a first means on the flexible elongate member for sealing a duct.

3. A thermal ablation catheter as in claim 2, wherein said sealing means is disposed proximally on the heating means.

4. A thermal ablation catheter as in claim 2, wherein said sealing means is disposed distally of the heating means.

5. A thermal ablation catheter as in claim 2, further comprising a second means for sealing a duct disposed on the flexible elongate member, wherein the first and second sealing means are located on opposite sides of the heating means.

6. A thermal ablation catheter as in claim 1, wherein the heating means extends over a predetermined length of at least about 3 mm.

7. A thermal ablation catheter as in claim 6, wherein the heating means is formed substantially continuously over said predetermined length.

8. A thermal ablation catheter as in claim 6, wherein the heating means is discontinuously distributed over said axial length.

9. A thermal ablation catheter as in claim 2, wherein at least a portion of the length of the heating means is disposed within the first sealing means.

10. A thermal ablation catheter as in claim 6, wherein the heating means provides a non-linear heat flux pattern along its predetermined length, said pattern being selected to provide a desired heating profile within the fluid environment.

11. A thermal ablation catheter as in claim 10, wherein the heating means includes at least two spaced-apart discrete heating elements, wherein the spacing is selected to provide a desired heating pattern.

12. A thermal ablation catheter as in claim 1, wherein the heating means includes a coil wrapped about the exterior of the elongate member over said predetermined length.

13. A thermal ablation catheter as in claim 12, wherein the pitch of the coil is varied along the length of the elongate member in order to provide a non-linear heat flux pattern selected to provide a desired heating profile within the fluid environment.

14. A thermal ablation catheter comprising:
    a flexible elongate member having proximal and distal ends; and
    a heating coil wrapped externally over a predetermined length of the elongate member near its distal end wherein the spacing between adjacent winding of the coil is varied in order to provide a preselected non-linear heat flux pattern.

15. A thermal ablation catheter as in claim 14, wherein the predetermined length is in the range from about 3 mm to 6 cm.

16. A thermal ablation catheter as in claim 14 further comprising a first inflatable balloon on the flexible elongate member for sealing a duct and a means on the elongate member for selectively inflating said balloon.

17. A thermal ablation catheter as in claim 16, wherein the first inflatable balloon is disposed distally of the heating coil.

18. A thermal ablation catheter as in claim 16, wherein the first inflatable balloon is disposed proximally of the heating coil.

19. A thermal ablation catheter as in claim 16, further comprising a second inflatable balloon on a side of the heating coil opposite to that of the first inflatable balloon.

20. A thermal ablation catheter as in claim 16, further comprising means for heating an inflation medium within the inflatable balloon.

21. A thermal ablation catheter as in claim 16, wherein the means for heating comprises a portion of the heating coil which extends beneath the inflatable balloon.

22. A thermal ablation catheter, said catheter comprising:
    an elongate member having proximal and distal ends;
    means on the elongated member for introducing an unconstrained thermally conductive medium into a fluid environment surrounding the distal end of the elongate member; and
    means on the elongate member for heating the unconstrained thermally conductive medium in the fluid environment surrounding the distal end of the elongate member to a temperature sufficient to destroy tissue in contact with the unconstrained medium.

23. A catheter as in claim 47, wherein the elongate member is flexible.

24. A catheter as in claim 22, wherein the means for heating the fluid environment comprises a convective heating element exposed to said fluid environment and means for raising the surface temperature of the heating element.

25. A catheter as in claim 49, wherein the convective heating element is a resistive heating element and the means for raising the surface temperature includes circuitry for supplying current to the resistive heating element.

26. A catheter as in claim 49, wherein the convective heating element is a heat conductive block and the means for raising the surface temperature includes an optical waveguide for supplying radiation to heat the block.

27. A catheter as in claim 24, further comprising an axial passage in the convective heating element and an axial lumen in the elongate member, wherein the axial passage in the heating element is contiguous with the axial lumen in the elongate member.

28. A catheter as in claim 47, wherein the means for heating includes a radiofrequency generator.

29. A catheter as in claim 28, wherein the radiofrequency generator for heating is a microwave generator.

30. A catheter as in claim 47, further comprising a cage surrounding the means for heating to prevent direct contact of the means for heating with the interior of a hollow body organ while allowing substantially unrestricted exposure of the means for heating to the surrounding fluid environment.

31. A catheter as in claim 47, further comprising first means at the distal end for sealing a duct which could otherwise drain fluid from the hollow body organ.

32. A catheter as in claim 31, further comprising means for heating the duct sealing means.

33. A catheter as in claim 56, wherein the sealing means is an inflatable balloon and the catheter further comprises a means on the elongate member for selectively inflating said balloon.

34. A catheter as in claim 58, further comprising means for heating an inflation medium within the inflatable balloon.

35. A catheter as in claim 22, wherein the means for introducing an unconstrained thermally conductive medium is a lumen which directs the medium past the means for heating and into the fluid environment.

36. A catheter as in claim 47, further comprising means for aspirating fluid from the fluid environment surrounding the distal end of the elongate member.

37. A thermal ablation catheter, said catheter comprising:
a flexible elongate member having proximal and distal ends;
a first inflatable balloon disposed about the elongate member near its distal end;
means on the elongate member for selectively inflating the balloon;
means on the elongate member for introducing a thermally conductive medium to a fluid environment surrounding the distal end of the elongate member, said introducing means being disposed on one side of the inflatable balloon; and
means for heating the thermally conductive medium in the fluid environment surrounding the distal end of the elongate member, said heating means being disposed on the same side of the first balloon as is the introducing means and being capable of conforming to flexure of the elongate member.

38. A thermal ablation catheter as in claim 37, further comprising at least one additional inflatable balloon disposed on a side of the heating means opposite to that of the introducing means and the first inflatable balloon.

39. A thermal ablation catheter as in claim 37, wherein the heating means includes at least one discrete heating element disposed proximally to the first balloon.

40. A thermal ablation catheter as in claim 37, wherein the heating means includes at least one discrete heating element disposed distally to the first balloon.

41. A thermal ablation catheter as in claim 37, wherein the heating means provides a non-linear heat flux pattern over a predetermined axial length, said pattern being selected to provide a desired heating profile within the fluid environment.

42. A thermal ablation catheter as in claim 41, wherein the predetermined axial length of the heating means is in the range from about 3 mm to 6 cm.

43. A thermal ablation catheter as in claim 37, wherein the heating means includes a plurality of spaced-apart heating elements, wherein the spacing is selected to provide a desired heating pattern.

44. A thermal ablation catheter as in claim 37, wherein the heating means includes a coil wrapped about the exterior of the elongate member.

45. A thermal ablation catheter as in claim 44, wherein the pitch of the coil is varied along the length of the elongate member in order to provide a non-linear heat flux pattern over a predetermined axial length.

46. A method for ablating a hollow body organ having at least one connecting duct, said method comprising the following steps performed in a predetermined order:
sealing the connecting duct;
introducing a thermally conductive medium into the hollow body organ;
heating a portion of the connecting region to a temperature and for a time sufficient to destroy the endothelial lining or mucosa of said portion; and
heating the thermally conductive medium within the hollow body organ to a temperature and for a time sufficient to destroy the endothelial lining mucosa of the hollow body organ.

47. A method as in claim 46, wherein heating of the connecting region is performed prior to heating of the hollow body organ.

48. A method as in claim 46, wherein heating of the connecting duct and heating of the hollow body organ are performed substantially simultaneously.

49. A method as in claim 46, wherein heating of the connecting duct is performed after introducing the thermally conductive medium but prior to heating the thermally conductive medium within the hollow body organ.

50. A method as in claim 46, further comprising introducing a thermally conductive medium into the connecting duct prior to introducing the medium into the hollow body organ.

51. A method as in claim 50, wherein thermally conductive medium is introduced substantially simultaneously to both the connecting duct and the hollow body organ after the connecting duct is sealed.

52. A method as in claim 50, wherein thermally conductive medium is introduced to the connecting duct prior to heating the connecting duct and is introduced to the hollow body organ thereafter, followed by heating of the hollow body organ.

53. A method as in claim 46, wherein sealing of the connecting region includes inflating a balloon to occlude the connecting duct.

54. A method as in claim 53, wherein heating of the connecting duct includes heating of an inflation medium within the balloon.

55. A method as in claim 53, wherein the inflation medium is heated to a temperature in the range from about 45° C. to 120° C.

56. A method as in claim 53, wherein a region of the connecting duct proximal to the balloon is heated.

57. A method as in claim 46, wherein the thermally conductive medium is substantially unheated when introduced into the hollow body organ.

58. A method as in claim 46, wherein the thermally conductive medium is heated to a temperature in the range from about 45° C. to 120° C. for a time in the range from about 1 minute to 60 minutes.

59. A method as in claim 57, wherein the hollow body organ is the gallbladder and the connecting duct is the cystic duct.

* * * * *